United States Patent [19]

Gilberto

[11] Patent Number: 4,535,623
[45] Date of Patent: Aug. 20, 1985

[54] MATERIAL HARDNESS TESTING APPARATUS

[76] Inventor: Paul Gilberto, 145 Carmen Rd., Milford, Conn. 06460

[21] Appl. No.: 608,995

[22] Filed: May 10, 1984

Related U.S. Application Data

[63] Continuation of Ser. No. 465,756, Feb. 11, 1983, abandoned, which is a continuation of Ser. No. 231,108, Feb. 3, 1981, abandoned, which is a continuation of Ser. No. 18,816, Mar. 8, 1979, abandoned.

[51] Int. Cl.³ .............................................. G01M 3/42
[52] U.S. Cl. ........................................... 73/81; 73/83
[58] Field of Search ................... 73/81, 82, 83, 862.53; 269/241; 254/102

[56] References Cited

U.S. PATENT DOCUMENTS

| | | | |
|---|---|---|---|
| 873,248 | 12/1907 | Lagasse et al. | 254/102 |
| 1,770,046 | 7/1930 | Shore | 73/81 |
| 1,886,851 | 11/1932 | Trecker | 252/102 |
| 3,123,997 | 3/1964 | Cosner | 73/81 |
| 3,123,998 | 3/1964 | Newman | 73/83 |
| 3,128,621 | 4/1964 | Scott | 73/81 |
| 3,352,148 | 11/1967 | Shore | 73/81 |
| 3,406,566 | 10/1968 | Livingston et al. | 73/81 |
| 3,486,373 | 12/1969 | Scott | 73/141 |
| 3,589,708 | 6/1971 | Cosner | 269/241 |
| 3,628,376 | 12/1971 | Dega et al. | 73/89 |
| 3,728,551 | 4/1973 | Culver et al. | 250/231 SE |
| 3,754,436 | 8/1973 | Saxton | 73/81 |
| 3,815,125 | 6/1974 | May et al. | 340/347 P |
| 4,075,478 | 2/1978 | Walker | 250/231 SE |
| 4,094,188 | 6/1978 | Bellouin et al. | 73/81 |
| 4,147,052 | 3/1979 | Tsujiuchi et al. | 73/81 |
| 4,175,428 | 11/1979 | Eilersen | 73/141 |
| 4,182,166 | 1/1980 | Herr | 73/134 |
| 4,193,199 | 3/1980 | Whiteley | 33/1 PT |
| 4,195,494 | 3/1980 | Kinney | 64/9 R |
| 4,199,976 | 4/1980 | Edward | 73/81 |
| 4,222,262 | 9/1980 | Batie et al. | 73/81 |
| 4,304,123 | 12/1981 | Achinger et al. | 73/81 |
| 4,312,220 | 1/1982 | Borgerson et al. | 73/81 |
| 4,312,221 | 1/1982 | Edward et al. | 73/81 |
| 4,380,926 | 4/1983 | Fritts et al. | 73/83 |

*Primary Examiner*—S. Clement Swisher
*Attorney, Agent, or Firm*—F. Eugene Davis, IV

[57] ABSTRACT

The surface hardness of material is tested by the extent of penetration of a tool thereinto by moving the tool onto the surface from a low to a high value of compressive force and then back to the low value by reversible rotative movements with the penetration being determined from the difference between the two rotative movements, in which the movement may be related to incremental rotative steps with the difference in the number of steps determining the extent of penetration and in which the movement may be automatically performed. The improvements comprise differential thread means comprising a rotatable part and means for revolving the rotatable part to effect linear movement of the penetrating end, and flexure means allowing free axial motion but preventing rotation of the rod (21) therebetween.

19 Claims, 4 Drawing Figures

MATERIAL HARDNESS TESTING APPARATUS

This application is a continuation of application Ser. No. 465,756, filed Feb. 11, 1983, now abandoned, which is a continuation of application Ser. No. 231,108, filed Feb. 3, 1981, now abandoned, which was a continuation of Ser. No. 018,816, filed Mar. 8, 1979, now abandoned.

The present apparatus has particular utility when employed to determine the hardness of the surface of material such as its Rockwell number or Brinnell number. The hardness is related to the depth of penetration of a penetrator or tool end into the surface when a selectable value of compressive force is applied to the tool. In heretofore known Rockwell type hardness testing apparatus, the force that is exerted on the tool is produced by gravity acting on weights and this in turn is transferred by mechanical devices to the tool. The depth of penetration is generally directly measured from the tool and displayed on a dial indicator, digital display, etc. While such heretofore known apparatus have operated, the dependence of gravity acting on weights and the measurement of the tool movement has rendered them somewhat expensive, relatively large and subject to impreciseness.

It is accordingly an object of the present invention to provide a penetrating hardness tester which is relatively economical to manufacture, quite compact, less subject to error than heretofore existing machines but yet is quite precise in providing a measure of the hardness.

Another object of the present invention is to achieve the above object by a hardness testing apparatus and method which utilizes rotative movements to effect penetration of the tool and in which the depth of penetration is derived from the difference in the extents of reversible rotary movements.

A further object of the present invention is to provide a hardness testing apparatus and method which is capable of automatic operation to provide a measure of the depth of penetration which may be converted to a standard hardness designation.

Still another object of the present invention is to provide an apparatus and method which is usable to test a wide range of materials and which is adaptable for manufacture in a number of different sizes and resolutions.

In carrying out the present invention, there is provided an anvil or platform on which the material to be tested is positioned. Spaced from the platform is a frame which supports a tool supporting means with the latter carrying the penetrating tool at one end and a threaded portion at its other end. The threaded portion is supported by the frame through a differential thread means so that a rotative movement applied to the differential thread means causes the tool to be linearly movable. A compressive force indicating means is positioned between the threaded portion and the tool to provide signals indicating the value of the compressive force being applied by the tool onto the surface of the material.

In accordance with the present apparatus and method, a rotative movement is applied to the differential thread means until the tool engages the surface of the material with a selected low value of compressive force as measured by the compressive force measuring means. A further rotative force in the same direction is applied until a selectable high value of compressive force is exerted by the tool and indicated by the measuring means. A reverse rotational movement is then effected until the same value of low compressive force is measured. By determining the extent of the first rotative movement from the low to high compressive force values and subtracting therefrom the extent of the reverse rotative movement from the high to the low values, the rotative difference in the extent of the two movements is obtained. From the difference and utilizing the translation ratio of the differential thread means, the linear depth of penetration may be manually or automatically accordingly computed. By having the penetration, the hardness of the material then becomes known by using a table for the specific tool employed.

Other features and advantages will hereinafter appear.

Figure 1:
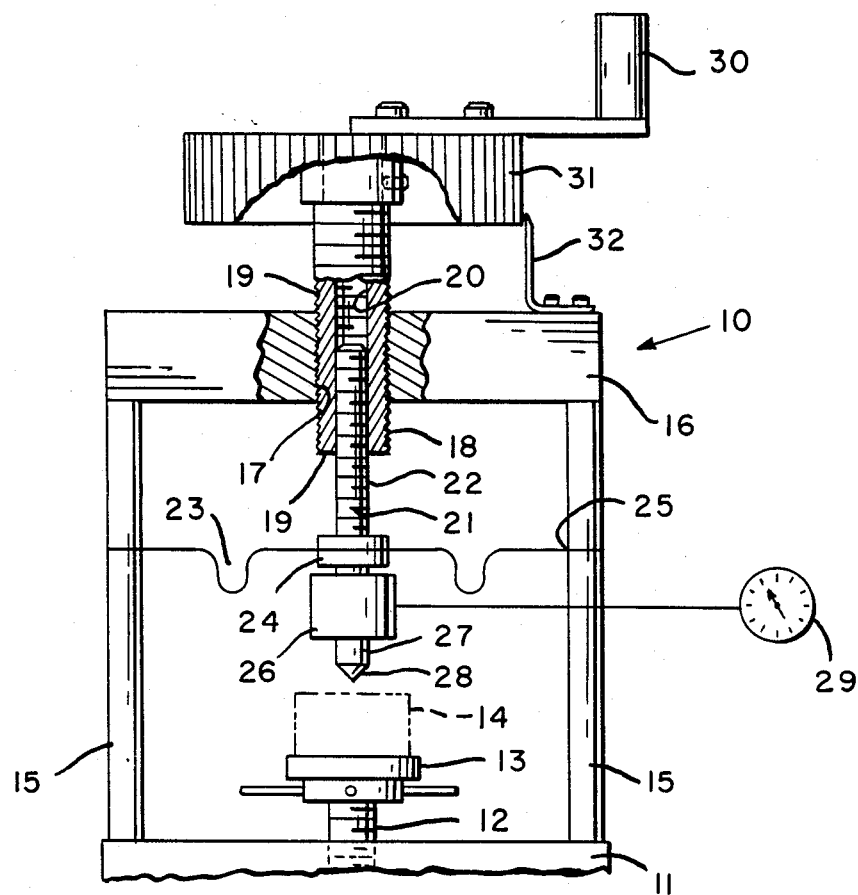
FIG. 1 is an elevation partly in section of one embodiment of the present invention.

Referring to the drawing, the hardness testing apparatus disclosed is generally indicated by the reference numeral 10 and includes a base 11. A threaded member 12 is rotatably supported in the base 11 and carries a platform 13 at its upper end on which a piece of material 14, shown in dotted lines, is adapted to be positioned to have its hardness determined.

In the specific embodiment shown, a pair of uprights 15 are secured to the base 11 in any convenient manner with a cross-member 16 being fixed thereto to extend therebetween and be spaced above the platform. While two uprights are shown, it is generally preferable to employ only one upright located at the rear of the apparatus in order to maximize the accessibility to the platform. A threaded aperture 17 is formed in the cross-member and its threads cooperate with the exterior threads 18 of a tubular member 19 which is also interiorly threaded as at 20. A rod 21 is positioned within the tubular member and has exterior threads 22 which cooperate with the interior threads 20. (For preventing rotation of the rod 21 while permitting unhampered linear movement, a flexure plate 23 has its inner periphery secured to the rod as at 24, while its outer periphery is secured to the supports 15 as at 25.)

The lower end of the rod 21 is fixed to one side of a compressive force measuring means 26, sometimes conveniently referred to as a "load cell" as indicated in the drawing, while the other side of the load cell carries a tool 27 having a penetrating end 28. In the embodiment shown in FIG. 1, a visual extent of the compressive force is provided by a meter 29 connected to receive the signal from the load cell. One form of compressive force measuring means that may be employed is model No. 3132, available from Lebow Assoc., Inc., 1728 Maplelawn Road, Troy, Mich. and which has a capacity of 500 lbs.

The penetrating end 28 is linearly moved with respect to the surface of the material 14 by rotation of a crank 30 secured to the tubular member 19. A circular graduated scale 31, preferably graduated in an even number of equal increments or steps per revolution, such as 200, is also connected to the tubular member and cooperates with a pointer 32 fixed to the cross-member 16.

The threads 17 and 18 and the threads 20 and 22 comprising a differential screw or differential thread means, are similarly inclined but have slightly different pitches with one example being 16.4 threads per inch for one thread and 16 threads per inch for the other. With these specific pitches, one rotation of the tubular member will cause the rod to move a linear distance of 0.0015224 inches (1/16–1/16.4). If the scale 31 is graduated in 200 equal steps, then each step will be equal to 7.6 millionths (0.0000076) inches, which is generally well within the desired resolution of a hardness testing apparatus. For a one point Rockwell hardness difference between C62-63, a difference of only 80 millionths (0.000080) inches is required. It will, of course, be understood that the above numerical examples are merely exemplary and other differential thread ratios and scale graduations may be employed depending upon the desired resolution for each rotative increment.

In the operation of the present apparatus, the material 14 is positioned on the platform 13 and the height of the platform is adjusted to position the upper surface of the material within the linear operating range of the penetrating end 28. The crank 20 is rotated to linearly move the tool towards and onto the upper surface until a selected low value of compressive force is indicated on the meter 29, as for example 10 kgf. A reading of the scale 31 at the pointer is then recorded. The crank is then again rotated in the same direction until a high selected value of compressive force is indicated on the meter 29, as for example 150 kgf. After a short pause, the crank is turned in the opposite direction to move the tool away from the work until the meter indicates again a value identical to the low initial compressive force. A second reading of the scale at the pointer is again made and its value is subtracted from the first reading to obtain the number of rotative increments that the end 28 has penetrated the material. This difference in rotative increments is multiplied by the linear movement per increment to obtain the linear depth penetration. In conventional fashion, the penetration may be converted to a Rockwell hardness or other hardness, number by the use of a table that is set by the characteristics of the penetrating end 28.

Figure 2:
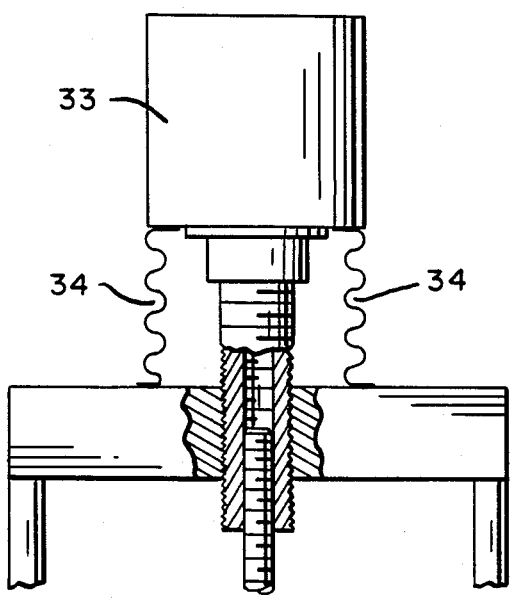
FIG. 2 is an elevation of a portion of FIG. 1 showing a further embodiment thereof.
Figure 3:
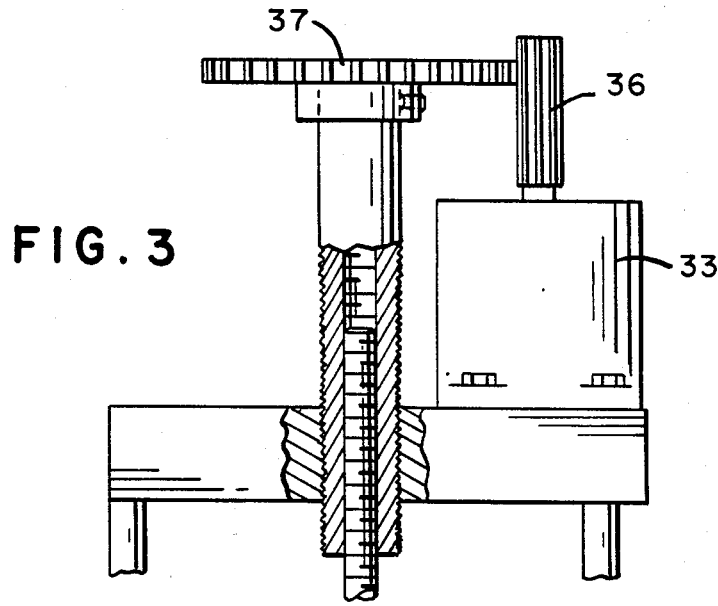
FIG. 3 is a view, similar to FIG. 2, of still another embodiment.

In the embodiment of the invention shown in FIGS. 2 and 3, the crank 30 is replaced by a stepping motor of the type that produces a plurality of equal length steps per revolution, such as two hundred, is capable of stopping at each step and is reversible. One type of motor that may be employed is available under the trademark "Slo-Syn" from The Superior Electric Company, Bristol, Conn. In the FIG. 2 embodiment, the motor 33 is directly connected to the end of the tubular member 19 and is shown supported above the cross-member 16 by a pair of linearly flexible elements 34. The latter elements enable the motor to move linearly with the tubular member with respect to the frame but prevent relative rotational movement with respect thereto. One form of elements that may be used are sections of or a complete tubular bellows.

The stepping motor 33 in the FIG. 3 embodiment is shown directly bolted to the cross-member 16 and the shaft of the motor carries an elongate pinion gear 36 that meshes with a spur gear 37 secured to the end of the tubular member 19. The elongate pinion accommodates linear movement of the tubular member. In this embodiment, the ratio of the gears enters into the determination of the linear movement of the tool end for each step of the motor.

Figure 4:
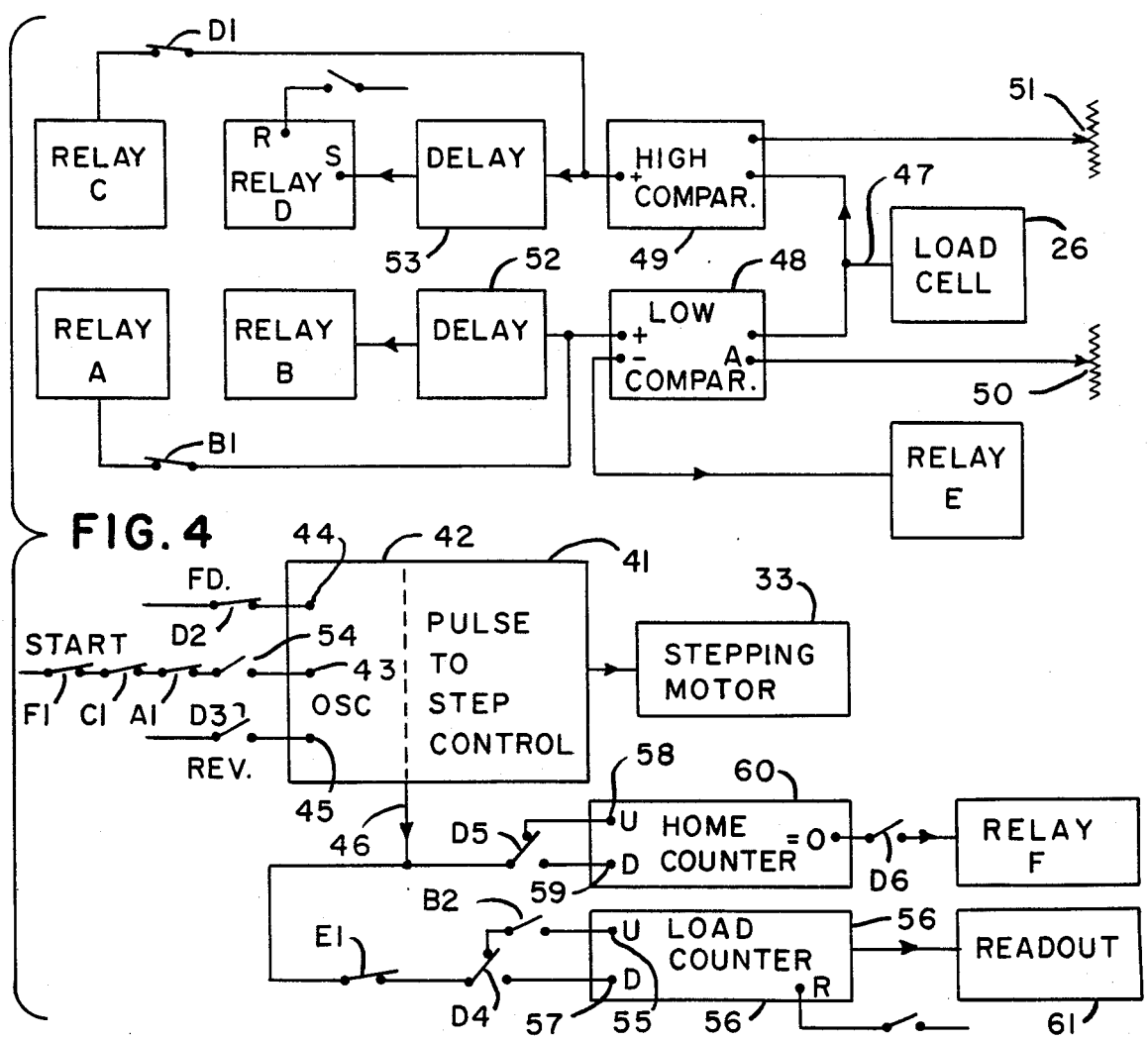
FIG. 4 is an electrical block and schematic diagram for providing automatic operation of the FIG. 2 or FIG. 3 embodiments.

The motor 33 may be manually controlled if desired and the difference in rotative movement determined by the scale 31 or by electrically counting the number of steps the motor moves. However, it is preferred that the motor be automatically operated and shown in FIG. 4 is an electrical block and schematic diagram of a circuit for automatically controlling the stepping motor to perform the method of the present invention and provide a digital or other readout of the depth of penetration. The movement of the stepping motor 33 is controlled by a pulse to step control 41 which includes an oscillator 42 for producing pulses. The control 41 has a start terminal 43 together with a forward direction terminal 44 and a reverse direction terminal 45. Upon energization of the start terminal 43, the oscillator will produce pulses with the motor being energized by the control to produce one increment of rotational movement or step for each pulse produced with the direction being set by which direction terminal receives energization. Pulses are also directed outwardly of the control on a lead 46.

One form of motor control that may be employed is available from The Superior Electric Company, Bristol, Conn. with a type STM 1800CV being specifically usable to control a type MO92-FD09 stepping motor.

The relays of FIG. 4 are identified by capital letters A, B, C, etc. and their respective switches by capital letters and subscript $A_1$, $B_2$, $B_1$, $B_2$, $C_1$, $C_2$, etc.

The load cell 26 produces a signal voltage related to the value of the compressive force and it is directed on a lead 47 to both a low voltage comparator 48 and a high voltage comparator 49 with the former also receiving a settable low value voltage from an adjustable resistor 50 that is adapted to be connected across a source of appropriate power while the high voltage comparator also receives a settable high value voltage from the setting of a high adjustable resistor 51. The + output of the low comparator energizes a relay A through a switch B1 of a relay B which is also energized by the + output of the comparator after a delay 52. Further, a relay E is connected to be also energized by the − output of the low comparator 48.

The + output of the high comparator 49 is directed through a switch D1 of relay D to energize a relay C and also after a delay 53, to energize the set (S) terminal of latching relay D that is reset by applying a reset signal to its R terminal.

The pulses on the lead 46 are directed through switches E1, of relay E D4 of relay D and B2 of relay B to the count up terminal 55 of a load difference digital counter 56 whose count down terminal 57 is also connected to the other side of switch D4 of relay D. Further, the lead 46 pulses are directed to count up 58 and count down 59 terminals of a full range home digital counter 60 through a switch D5 of relay D. The counter 60 has a count equals zero terminal connected to energize a relay F through switch D6 of relay D.

Switch A1 of relay A is normally closed and connected in series with the start terminal 43 of the control 41 through a manually operable start switch 54 with switches C1 of relay C and F1 of relay F being connected in series therewith so that operation of the control requires that all switches be closed. The forward terminal 44 is energizable through a switch D2 of relay D while the reverse terminal is energizable through a switch D3 of relay D. All switches are shown in the open or closed position which they attain when their relays are deenergized.

In the operation of the system, the low level and the high level adjustable resistors 50 and 51 are set to desired values of compressive force, the delay 52 is set for a duration of 2 seconds, the delay 53 is set for a duration of 4 seconds, the platform adjusted to position the upper surface of the material 14 within the operating range of the tool and the reset lines have been cleared to unlatch relay D and set load counter 56 to a zero count. All relays except E are thus deenergized and both counters read zero with a zero reading of the counter 60 indicating that the tool is in its home or reset location. The start switch 54 is then closed to energize the control and the motor moves in a forward direction by switch D2 of relay D being closed and with the counter 60 counting up the steps from the home position. As switch E1 of relay E is open because the value of the signal from the load cell is less than the value of the signal from the resistor 50, the counter 56 does not receive pulses. When the load cell produces a force equal to the low value, the low comparator 48 produces a + output signal that energizes relay A through switch B1 of relay B which opens switch A1 of relay A to stop the motor. Relay E becomes deenergized. After expiration of the delay 52, the relay B becomes energized, deenergizing relay A by switch B1 of relay B opening to again energize the oscillator. The switch B2 of relay B becomes closed so that the load counter 56 counts up to the pulses received on the lead 46 and hence the steps produced by the motor as the tool is pressed against the material 14 surface by the pulses passing through switches E1 of relay E, D4 of relay D and B2 of relay B.

Upon the load cell providing a signal of a compressive force equal to that set by a high level adjustable resistor 51, the high comparator 49 produces an output which energizes the relay C to open switch C1 thereof to stop the oscillator and hence the motor. Upon expiration of the duration of the delay 53, the latching relay D is energized to deenergize relay C to start the oscillator, to open switch D2 of relay D and close switch D3 thereof to enable energizing the motor in the reverse direction, switch D4 thereof shifts to apply the pulses for each reverse step to the down terminal 57 of the counter 56 to decrease the counter count, switch D5 thereof shifts the pulses to the down terminal of counter 60 and switch D6 thereof readies relay F for energization. The motor moves reversely and the counters 56 and 60 are down counted for each step until the load cell again produces a signal which is equal to the value set by the low adjustable resistor 50. At this time, the low comparator 48 signal shifts to deenergize relay E to stop the load counter 56 from counting further pulses. The motor is maintained energized in the reverse direction until it reaches its home position when counter 60 attains a zero count and energizes relay F to open switch F1 thereof and stop the motor.

The counter 56 accordingly has a numerical count that is the difference in incremental rotational steps between the low to high value movement in a forward direction and the high to low value movement in the reverse direction. The numerical count in the counter may be displayed if desired on a digital readout 61 as steps or may be computed using conventional techniques into a depth of penetration in inches or may be computed to a hardness number, if desired.

The stepping motor is preferably operated at a speed less than 500 steps per second so that the relay E can react without error. However, if desired, the system may be stopped for a short duration after returning to the low load position as by adding another delay and relay to the circuit, if necessary.

It will accordingly be understood that there has been disclosed a hardness tester which measures the depth of penetration of a tool end into the material to be tested. The tool end is linearly moved against the material until a low value of compressive force is attained and then reversely moved to the same low force. The tool end is moved by a rotational motion acting through a differential thread and the extent of penetration is determined by the difference in the rotational movements rather than the linear movement of the tool. The difference in extent is measured by the number of incremental steps which is then computable into the linear depth penetration. While the apparatus may be operated manually, it is preferably operated by a stepping motor which produces equal length incremental steps and the extent of the difference movement is measured by the difference in the number of step commands supplied the motor.

Variations and modifications may be made within the scope of the claims and portions of the improvements may be used without others.

I claim:

1. In an apparatus for testing the hardness of material comprising a rigid platform on which the material is adapted to be positioned, a frame spaced from the platform, means mounted on the frame for linear movement towards and away from the platform, said means comprising an end part (21) adjacent the platform and having a penetrating end (28) adapted to engage the surface of the material (14) and an other end (20) adjacent the frame 16, compressive force measuring means (26, 29) for indicating the force exerted by the penetrating end on the material, and penetrating motion measuring means (31, 32) for indicating the penetrating motion of the penetrating end into the material, the improvement comprising:

differential thread means comprising a rotatable part (18) having a pair of coaxial threads (19, 19) of different pitches formed thereon; means (17) on the frame (16) engaging the threads of one pitch; means on the other end (20) of the end part (21) engaging the threads of another pitch; means (30) for revolving the rotatable part to effect linear movement of the penetrating end, and flexure means (23) connected between the frame 15 and the end part allowing free axial motion between said frame and said end part but preventing relative rotation therebetween.

2. The invention as defined in claim 1 in which said rotatable part is a tubular member having inner and outer threads, said inner and outer threads being said pair of coaxial threads of different pitches.

3. The invention as defined in claim 1 in which the penetrating motion measuring means comprises indicating means (31, 32) for providing an indication of the extent of revolvement of the differential thread means.

4. The invention as defined in claim 3 in which the means for revolving said rotatable part comprises a manually operable crank and said indicating means comprises a mark carried by the frame and a graduated scale interconnected with the differential thread means.

5. The invention as defined in claim 3 in which the means for revolving the differential thread means comprises a reversible stepping motor providing a fixed number of essentially spaced steps per revolution and in which the indicating means measures the amount of rotative movement by the number of steps produced by the stepping motor.

6. The invention as defined in claim 1 in which the compressive force measuring means comprises means for providing a high signal when a selectable high value of compressive force occurs.

7. The invention as defined in claim 6 in which the compressive force measuring means comprises means for providing a low signal when a selectable low value of compressive force occurs.

8. The invention as defined in claim 1 in which the means for revolving the differential thread means comprises a reversible stepping motor providing a fixed number of essentially equal steps per revolution, in which the compressive force measuring means produces a high signal when a selected high value of compressive force occurs and control means for energizing the motor in a direction to move the end towards the material and for stopping the movement upon the occurrence of the high signal.

9. The invention as defined in claim 8 in which the control means comprises means for reversing the direction of motor movement after the occurrence of the high signal.

10. The invention as defined in claim 9 in which the compressive force measuring means provides a low signal upon the occurrence of a low compressive force and in which the control means stops actuation of the motor for a short delay upon the occurrence of the low signal.

11. The invention as defined in claim 10 in which there are means for counting the number of steps that occur between a first low signal and a high signal and the same high signal and the next low signal and producing a count of the numerical difference therebetween in steps.

12. The invention as defined in claim 1 in which the means for revolving the rotatable part is an electric motor mounted to the frame and a spur gear mounted to the shaft, and an elongated pinion gear engaged therewith, rotated by the motor.

13. The invention defined in claim 1 and an electric motor comprising an output shaft, the output shaft connected directly to the rotatable part of the differential thread means, and the body of the motor connected to said frame means by additional means, allowing free axial movement therebetween, but preventing rotation therebetween.

14. The invention as defined in claim 13 in which the means for revolving the differential thread means comprises a reversible motor, and further means providing a signal indicating the position of the penetrating end, in which the compressive force measuring means produces a high signal when a selected high value of compressive force occurs and control means for energizing the motor in a direction to move the end towards the material and for stopping the movement upon the occurrence of the high signal.

15. The invention as defined in claim 14 in which the control means includes means for reversing the direction of motor movement after the occurrence of the high signal.

16. The invention as defined in claim 15 in which the compressive force measuring means provides a low signal upon the occurrence of a selected low compressive force and in which the control means stops actuation of the motor for a short delay upon the occurrence of the low signal.

17. The invention as defined in claim 16 and means responsive to the position signals for indicating the motion of the penetrating end between a first low signal and a high signal and the same high signal and the next low signal.

18. The invention as defined in claim 17 in which the position signals are equally spaced pulses for equally spaced motion of the penetrating end and the means for indicating the motion of the penetrating end is a counter for counting the pulses.

19. The invention as defined in claim 13 wherein said additional means is a tubular bellows.

* * * * *